United States Patent [19]

Bernardi et al.

[11] 4,166,911
[45] Sep. 4, 1979

[54] PYRIDAZINYL-ERGOLINE COMPOUNDS HAVING NEUROLEPTIC ACTIVITY

[75] Inventors: Luigi Bernardi; Carlo Elli; Giovanni Falconi; Alberto Bonsignori, all of Milan, Italy

[73] Assignee: Farmitalia Carlo Erba S.p.A., Milan, Italy

[21] Appl. No.: 870,095

[22] Filed: Jan. 17, 1978

[30] Foreign Application Priority Data

Feb. 2, 1977 [GB] United Kingdom ............... 4302/77

[51] Int. Cl.$^2$ .................... C07D 457/02; A61K 31/50
[52] U.S. Cl. ...................................... 544/238; 546/67; 424/250
[58] Field of Search ................... 260/250 A, 250 AH; 544/238

[56] References Cited

U.S. PATENT DOCUMENTS

| 3,598,822 | 8/1971 | Anderson et al. | 260/250 A |
| 3,642,792 | 2/1972 | Bellasio | 260/250 A |
| 3,687,971 | 8/1972 | Shen et al. | 260/250 A |
| 3,856,799 | 12/1974 | Hoehn et al. | 260/250 A |
| 3,891,641 | 6/1975 | Pifferi | 260/250 A |
| 3,957,785 | 5/1976 | Arcari et al. | 260/256.4 C |
| 3,957,805 | 5/1976 | Fanshawe et al. | 260/250 A |
| 3,975,388 | 8/1976 | Hakim et al. | 260/250 A |

Primary Examiner—Mark L. Berch
Attorney, Agent, or Firm—Oblon, Fisher, Spivak, McClelland & Maier

[57] ABSTRACT

Pyridazinyl-ergoline compounds having neuroleptic activity are obtained by reacting an 8β-tosylmethyl ergoline with the sodium derivative of an amino-pyridazine or a mercaptopyridazine in a dipolar aprotic solvent.

6 Claims, No Drawings

PYRIDAZINYL-ERGOLINE COMPOUNDS HAVING NEUROLEPTIC ACTIVITY

BACKGROUND OF THE INVENTION

1. Field of the Invention

The present invention relates to new ergoline derivatives and to the process for their preparation. More particularly the present invention relates to the preparation of compounds of general formula I

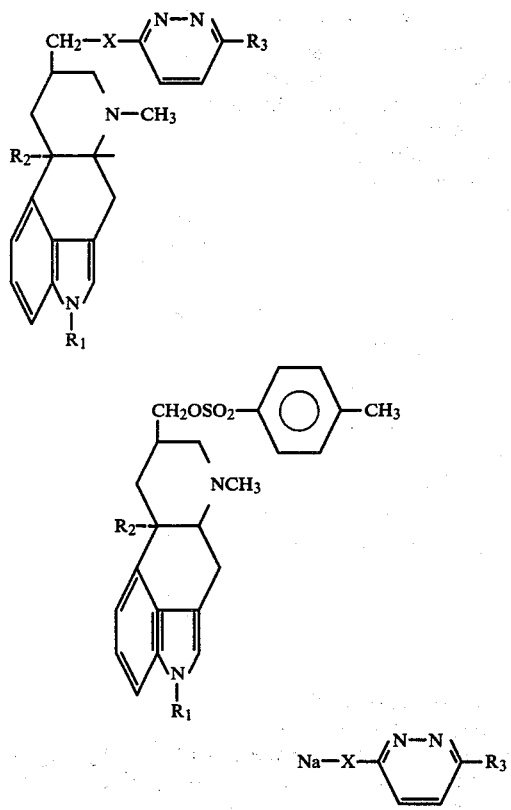

where $R_1$ can be H or $CH_3$, $R_2$ can be H or $OCH_3$, $R_3$ can be H, $CH_3$, OH, $CH_3O$, $CH_3S$, Cl, or Br, and X can be NH or S. The products of the present invention are formed by reacting the appropriate 8β-tosylmethyl ergoline II, where $R_1$ and $R_2$ have the above reported meanings with a compound of formula III in which X is as above defined, namely with the sodium derivative of the appropriate amino or mercaptopyridazine where $R_3$ has the above reported meaning, in a dipolar aprotic solvent such as dimethylsulfoxide, dimethylformamide, hexamethylphosphotriamide at a temperature of from 30° to 120° C. for 1 to 6 hours. The compounds are isolated as free bases or as salts of pharmaceutically acceptable acids.

The products of the present invention show a pharmacological activity hitherto unreported for ergoline derivatives, namely they are highly effective in protecting mice from the effects of administration of an otherwise lethal dose of amphetamine.

2. Description of the Prior Art

In 1957 L. Lasagna and W. P. McCann (Science, 125, 1241) reported that "tranquilizing" drugs, and particularly chlorpromazine, clearly reduce the amphetamine toxicity in aggregated mice. Subsequently many authors (C. D. Proctor et al., Arch. Int. Pharmacodyn., 1966, 163, 79; J. R. Boissier and P. Simon, Therapie, 1966, 21, 1491; D. E. Smith et al., Tox. Appl. Pharm., 1967, 10, 402; R. Cahen, C.R.S.B., 1968, 161, 2441) confirmed the activity of other neuroleptics in this test.

As far as we known this activity was never described for molecules belonging to the ergoline group.

DETAILED DESCRIPTION OF THE PREFERRED EMBODIMENTS

We recently submitted a large series of ergoline derivatives of general formula IV where X is NH or S and R a heteroaromatic residue

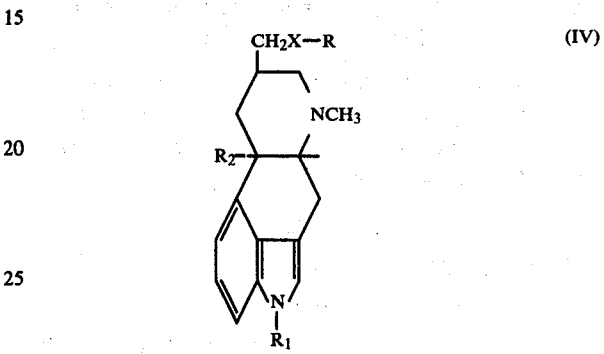

to the above test according to the following procedure:

The compounds, suspended in a 5% acacia pseudosolution, are intraperitoneally injected to male albino mice (22 g body weight). Twenty animals per group are treated with the test compounds at several dose levels and allocated in cages (cm 24×18×15 h) without food and water.

The control group is injected with the vehicle alone. One hour later all animals are intraperitoneally treated with 15 mg/kg of amphetamine sulfate. The death rate is registered after 24 hours, and the $ED_{50}$ value is calculated. In this condition all animals treated with amphetamine alone die within 24 hours. It has now been found quite surprisingly that among the ergolines of general formula IV only those compounds having the general formula I, where $R_1$, $R_2$, $R_3$ and X have the above reported meaning, show the ability to protect the aggregated mice from amphetamine toxicity, the $ED_{50}$ ranging from 16 to 30 mg/kg as reported in the following table:

| Compound | $ED_{50}$ |
|---|---|
| 355/902 | 16.4 |
| /903 | 30 |
| /904 | 30 |
| /914 | 16.7 |
| /927 | 30 |

Based on the above results it seems resonable to foresee for the new derivatives a clinical use in the symptomatic therapy of the functional psychosis responsive to the neutroleptics.

EXAMPLE 1

10-Methoxy-8β-(6'-chloro-3'-pyridazinylaminomethyl)-1,6-dimethyl-ergoline (355/902).

To a solution of 7.5 mmols of 3-amino-6-chloropyridazine in 30 ml of anhydrous dimethylformamide, 7.5 mmols of sodium hydride are added and the mixture stirred at 50° for 40 min. Subsequently 3.75 mmols of 10-methoxy-1,6-dimethyl-8β-tosylmethylergoline in 10 ml of dimethylformamide are added and the reaction mixture is kept at 50° for 3 hr. Evaporation of the solvent in vacuo leaves a residue that is first washed with pentane, then crystallized from acetone to give 10-methoxy-8β-(6'-chloro-3'-pyridazinylaminomethyl)-1,6-dimethylergoline, m.p. 215°-218° in 60% yield.

EXAMPLE 2

10-Methoxy-8β-(3'-pyridazinylaminomethyl)-1,6-dimethylergoline (355/904).

Operating as in example 1, but employing 3-aminopyridazine, 10-methoxy-8β-(3'-pyridazinylaminomethyl)-1,6-dimethylergoline, m.p. 262°-267° is obtained in 80% yield.

EXAMPLE 3

10-Methoxy-8β-(6'-methoxy-3'-pyridazinylaminomethyl)-1,6-dimethylergoline (355/903).

Operating as in example 1, but employing 3-amino-6-methoxypyridazine, 10-methoxy-8β-(6'-methoxy-3'-pyridazinylaminomethyl)-1,6-dimethylergoline, m.p. 228°-229°, is obtained in 72% yield.

EXAMPLE 4

10-Methoxy-1,6-dimethyl-8β-(6'-hydroxy-3'-pyridazinylmercaptomethyl)ergoline (355/914).

To a solution of 7.5 mmols of 6-mercapto-3-hydroxypyridazine in 40 ml of dimethylsulfoxide, 7.5 mmols of anhydrous sodium t-butylate are added and the solution is stirred at room temp. for 10 min. Subsequently 3.75 mmols of 10-methoxy-1,6-dimethyl-8β-tosylmethylergoline in 10 ml of dimethylsulfoxide are added and the solution stirred for 90 min. at 80°. Evaporation of the solvent in vacuo leaves a residue that is crystallized from acetone to give 10-methoxy-1,6-dimethyl-8β-(6'-hydroxy-3'-pyridazinylmercaptomethyl)ergoline, m.p. 216°-217° in 80% yield.

EXAMPLE 5

10-Methoxy-1,6-dimethyl-8β-(6'-chloro-3'-pyridazinylmercaptomethyl)ergoline (355/913).

Operating as in example 4, but employing 6-mercapto-3-chloropyridazine, 10-methoxy-1,6-dimethyl-8β-(6'-chloro-3'-pyridazinylmercaptomethyl)ergoline, m.p. 120°-123°, is obtained in 70% yield.

EXAMPLE 6

10-Methoxy-1,6-dimethyl-8β-(6'-methoxy-3'-pyridazinylmercaptomethyl)ergoline (355/916)

Operating as in example 4, but employing 6-mercapto-3-methoxy-pyridazine, 10-methoxy-1,6-dimethyl-8β-(6'-methoxy-3'-pyridazinylmercaptomethyl)ergoline, m.p. 114°-117°, is obtained in 82% yield.

EXAMPLE 7

10-Methoxy-1,6-dimethyl-8β-(3'-pyridazinylmercaptomethyl)ergoline (355/927)

Operating as in example 4, but employing 3-mercaptopyridazine, 10-methoxy-1,6-dimethyl-8β-(3'-pyridazinylmercaptomethyl)ergoline, m.p. 193°-194° is obtained in 80% yield.

What we claim is:

1. Pyridazinyl-ergoline compounds having the formula (I)

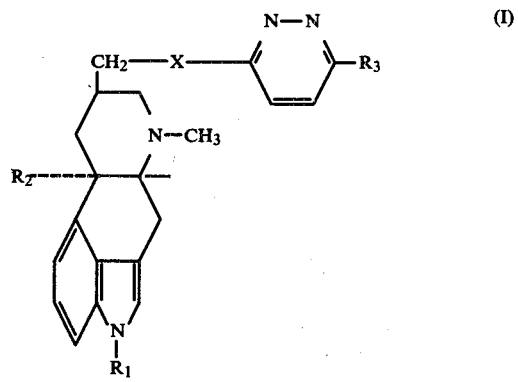

wherein
   $R_1$ is hydrogen or methyl;
   $R_2$ is hydrogen or methoxyl;
   $R_3$ is selected from the group consisting of hydrogen, methyl, hydroxyl, methoxyl, methylthio, Cl and Br; and
X is S.

2. The pyridazinyl ergoline compound of formula I according to claim 1, wherein $R_1$ is $CH_3$, $R_2$ is $OCH_3$, $R_3$ is $OCH_3$ and X is S.

3. The pyridazinyl ergoline compound of formula I according to claim 1, wherein $R_1$ is $CH_3$, $R_2$ is $OCH_3$, $R_3$ is H and X is S.

4. Salts of the pyridazinyl ergoline derivatives according to claim 1 with pharmaceutically acceptable acids.

5. The pyridazinyl ergoline compond of formula I according to claim 1, wherein $R_1$ is $CH_3$, $R_2$ is $OCH_3$, $R_3$ is OH and X is S.

6. The pyridazinyl ergoline compound of formula I according to claim 1, wherein $R_1$ is $CH_3$, $R_2$ is $OCH_3$, $R_3$ is Cl and X is S.

* * * * *